United States Patent [19]
Johnson et al.

[11] Patent Number: 5,304,141
[45] Date of Patent: * Apr. 19, 1994

[54] METHOD AND APPARATUS FOR INDUCING ANESTHESIA

[75] Inventors: Mark D. Johnson, Weymouth, Mass.; Vladimir Bittner, Bern, Switzerland

[73] Assignee: Brigham and Women's Hospital, Boston, Mass.

[*] Notice: The portion of the term of this patent subsequent to Aug. 3, 2010 has been disclaimed.

[21] Appl. No.: 624,750

[22] Filed: Dec. 31, 1990

Related U.S. Application Data

[63] Continuation-in-part of Ser. No. 448,321, Dec. 11, 1989, abandoned.

[51] Int. Cl.[5] .............................................. A61M 5/18
[52] U.S. Cl. ..................................... 604/158; 604/49; 604/164; 604/265
[58] Field of Search ............ 604/49, 51, 53, 158-170, 604/265, 266

[56] References Cited

U.S. PATENT DOCUMENTS

| | | |
|---|---|---|
| 1,527,291 | 2/1925 | Zorraquin . |
| 3,540,447 | 11/1970 | Howe . |
| 3,565,074 | 2/1971 | Foti . |
| 3,630,198 | 12/1971 | Henkin . |
| 3,780,733 | 12/1973 | Martinez-Manzor . |
| 3,782,381 | 1/1974 | Winnie . |
| 3,792,703 | 2/1974 | Moorehead . |
| 3,856,009 | 12/1974 | Winnie . |
| 4,230,123 | 10/1980 | Hawkins, Jr. . |
| 4,349,023 | 9/1982 | Gross . |
| 4,479,795 | 10/1984 | Mustacich et al. . |
| 4,518,383 | 5/1985 | Evans . |
| 4,650,472 | 3/1987 | Bates . |
| 4,653,475 | 3/1987 | Seike et al. ................. 604/165 |
| 4,700,694 | 10/1987 | Shishido . |
| 4,737,146 | 4/1988 | Amaki et al. . |
| 4,791,937 | 12/1988 | Wang ........................... 604/164 |
| 4,808,157 | 2/1989 | Coombs . |
| 4,846,799 | 7/1989 | Tanaka et al. . |
| 4,917,670 | 4/1990 | Hurley et al. . |
| 4,973,312 | 11/1990 | Andrew . |
| 5,015,238 | 5/1991 | Solomon et al. ............. 604/164 |
| 5,085,631 | 2/1992 | Leighton ..................... 604/164 |
| 5,160,323 | 11/1992 | Andrew ....................... 604/158 |

FOREIGN PATENT DOCUMENTS

| | | | |
|---|---|---|---|
| 197810 | 10/1978 | France . | |
| 0897224 | 1/1982 | U.S.S.R. ................. | 604/158 |

Primary Examiner—John D. Yasko
Assistant Examiner—Anthony Gutkowski
Attorney, Agent, or Firm—Sterne, Kessler, Goldstein & Fox

[57] ABSTRACT

The present invention provides apparatus and methods for introducing spinal anesthesia directly into the subarachnoid space of a patient. One apparatus and method utilizes a small gauge spinal needle for penetrating the dura; the other utilizes a small gauge catheter with an internal stylet having a non-piercing pencil point to spread apart the filaments of the dura wall. An introducer having a rounded tip is also provided for guiding and supporting the spinal needle or catheter, as force is applied thereto, to cause the same to penetrate the dura.

23 Claims, 2 Drawing Sheets

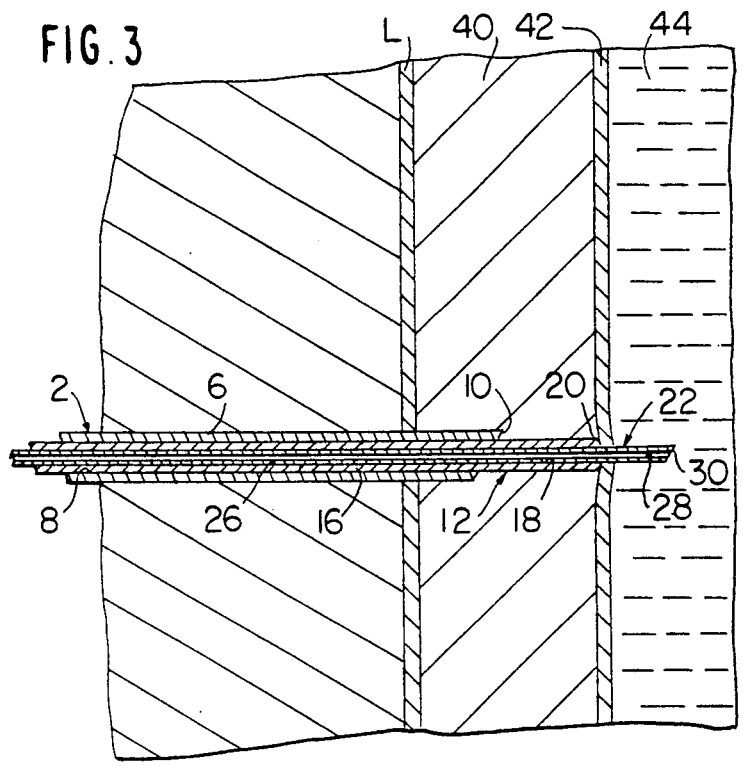
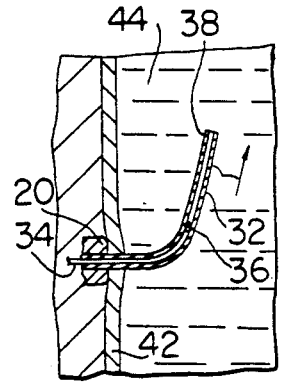
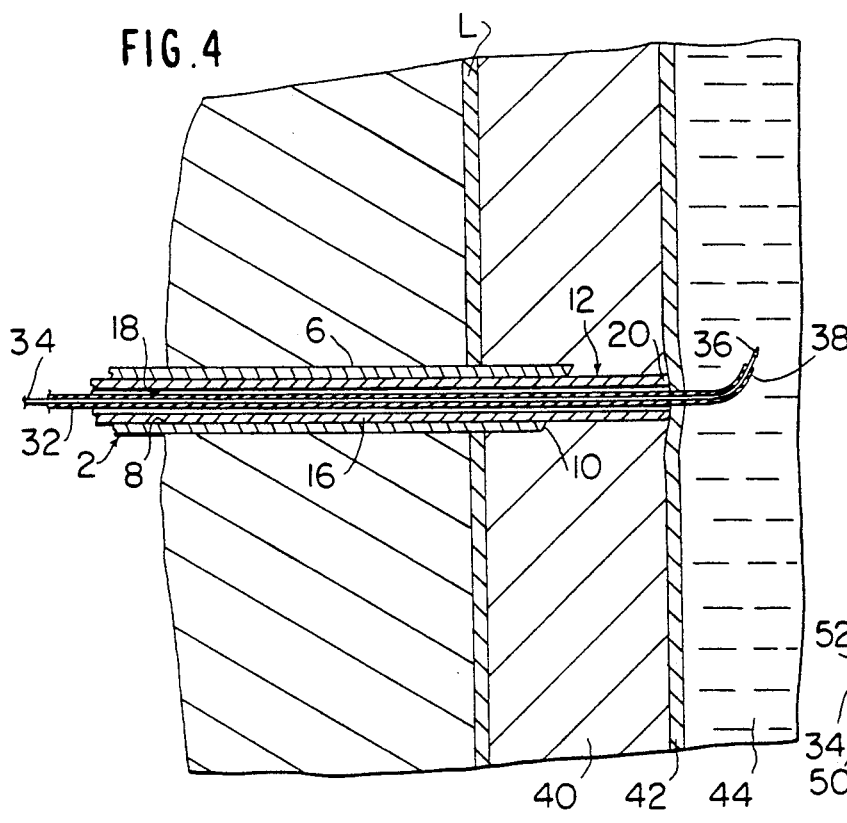
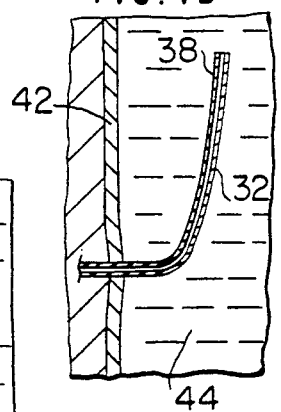
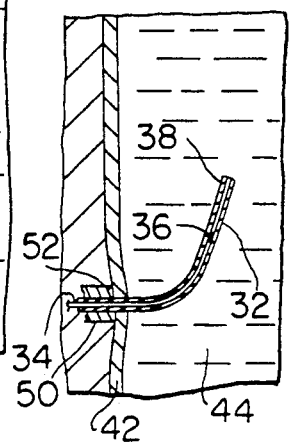

ions for the application of US Patent Number 5,304,141.

METHOD AND APPARATUS FOR INDUCING ANESTHESIA

RELATED APPLICATIONS

This application is a continuation-in-part of application Serial No. 448,321; filed Dec. 11, 1989 (abandoned).

FIELD OF THE INVENTION

The present invention is related to an apparatus and method for inducing anesthesia, and more particularly, to an improved apparatus and method for introducing local anesthetic agents and narcotics into the arachnoid and subarachnoid space through a relatively small opening.

BACKGROUND OF THE INVENTION

Apparatus and methods for introducing anesthesia to the spinal column have been available for many years. The majority of these methods and apparatus introduce anesthesia either by an epidural procedure, whereby the anesthesia is inserted into the epidural space via an epidural needle and catheter combination; or by a spinal procedure whereby the anesthesia is inserted through the dura itself into the subarachnoid space via a spinal needle.

An example of the epidural procedure is described in U.S. Pat. No. 4,349,023 to Gross. In this procedure, a sharp pointed hollow epidural needle is used to pierce the skin and spinal ligaments into the epidural space located between the ligaments and the dura. Catheter tubing is inserted through the lumen of the needle. The needle is removed and a syringe containing anesthesia is coupled to the distal end of the catheter. Anesthesia is provided to the patient via the syringe and catheter as needed throughout the medical procedure. This procedure allows the use of a relative large and steady epidural needle to insert the catheter. However, since the fluid is inserted into the epidural space, rather than directly into the subarachnoid space, the reaction time is relatively slow. Therefore, the procedure must be initiated a relatively long time before commencing surgery to ensure that the patient is sufficiently anesthetized. One advantage, however, of this procedure is that the precise amount of anesthesia necessary for the intended medical procedure, need not be determined, since the syringe or other device for storing the anesthesia may be replenished and thus administered continuously during the medical procedure.

The second common procedure for administering anesthesia is through a spinal needle, an example of which is described in U.S. Pat. No. 4,518,383 to Evans. In this procedure, a sharp pointed outer needle is pushed through the patient's skin and ligaments until it reaches the epidural space, stopping well before the dura wall to prevent damage thereto. A sharp pointed spinal needle is then inserted within the outer needle until it pierces the dura wall. A syringe containing anesthesia is coupled to the base of the spinal needle and anesthesia is transmitted from the syringe, though the spinal needle, directly into the dura. While this procedure is both simple and quick, it has been known to create what is referred to in the art as "spinal headache" a condition which results when punctures are made in the dura wall. It is believed that by reducing the size of the puncture made in the dura wall, the incidence of spinal headache may also be reduced. Thus, attempts have been made to reduce the gauge of the spinal needle, to thereby reduce the size of the puncture (gauge is measured by the outer diameter of the needle). However, as the needle gauge is reduced, the needle becomes so flexible and fragile that proper placement of the needle is extremely difficult. Moreover, since this procedure provides a "one shot" administration, that is, the needle is inserted and removed after the anesthesia is administered, the particular dosage of anesthesia required must be accurately determined before administration. Therefore, if the medical procedure continues for longer than that which was initially anticipated, it is possible that a second difficult insertion would have to be made in order to administer additional anesthesia. Such a result will significantly disrupt the medical procedure.

Recently, attempts have been made to combine the spinal and epidural procedures to provide both a controlled injection of anesthesia via a catheter, as well as to eliminate the incident of spinal headache by reducing the gauge of the instrument used to penetrate the dura and to administer the anesthesia. One example is described in U.S. Pat. No. 3,780,733 to Martinez-Manzor. This procedure provides a relatively large needle (15 gauge) for reaching the epidural space. A smaller gauge catheter with a 25 gauge needle on its end is inserted through the larger needle until it punctures the dura wall. A syringe containing anesthesia is connected to the distal end of the catheter. Anesthesia is then introduced directly into the dura through the catheter. One major problem with this procedure is that it is not suitable for use with very small gauge catheters, e.g., 28 gauge. This is because when unsupported, such fine gauge catheters are highly subject to breaking when the requisite amount of force required to puncture the dura is applied thereto. Furthermore, without guidance, it is very difficult to maneuver such fine gauge catheters within the body. Thus, it is extremely difficult to ensure proper placement.

To further minimize the incidence of spinal headache, it has also been proposed to insert a very small gauge catheter, typically a 32-gauge catheter, into the dura through a larger 26-gauge standard spinal needle which is used to puncture the dura. One problem with this procedure is that it creates a hole in the dura wall which is larger than the diameter of the catheter, thus minimizing the opportunity of a seal to be created between the catheter and the dura wall, and allowing the incidence of cerebral spinal fluid (CSF) leakage. Furthermore, while the incidence of spinal headache may be reduced by this procedure, it is not likely eliminated, since a 26-gauge needle is still of sufficient diameter to cause such. Moreover, a small 32-gauge catheter is extremely fragile and placement of the same has proven difficult at best. In addition, the lumen of this catheter is so small that it is easily susceptible to kinking which makes it impossible to transport anesthesia through the catheter. Thus, this method suffers from not only the problem of spinal headache, but also of difficult placement within the dura, resulting in a substantially unreliable procedure.

SUMMARY OF THE INVENTION

It is with these problems of the prior art in mind which the present invention was developed. The present invention not only overcomes the problems of the above-noted apparatus and procedures, but furthermore has many advantages not previously achieved in known apparatus and methods of anesthesia administration.

The present invention is directed to an apparatus for administering fluid into the body, comprising a first needle having a lumen and a pointed tip; an introducer having a hollow shaft and a non-piercing tip which is adapted to be inserted through the lumen of the first needle; and fluid carrying means for transporting fluid into the body, wherein the fluid carrying means is adapted to be inserted through the hollow shaft of the introducer. The fluid carrying means may be a spinal needle having a hollow shaft for transporting the fluid, and a sharp bevel point at one end. The fluid carrying means may alternatively comprise a catheter assembly including a catheter having a hollow interior for transporting the fluid.

Additionally, the present invention may also be characterized as a method for administering fluid into the body, comprising the steps of: inserting a needle into the body, the needle having a lumen; inserting an introducer into the lumen of the needle, the introducer having a hollow shaft and a non-piercing tip; guiding a fluid carrying means into the body by inserting the fluid carrying means into the hollow shaft of the introducer, the fluid carrying means having a penetrating point; causing the penetrating point to penetrate a desired region of the body; verifying placement of the penetrating point; coupling the fluid carrying means to a fluid source; and administering the fluid into the body. The method may further comprise the step of removing the needle from the body after placement of the penetrating point has been verified. The method may also comprise the step of removing the introducer from the body after the needle has been removed. Furthermore, the method may comprise the step of continuing to administer fluid into the body after the needle and introducer have been removed.

In addition, the present invention may be characterized as an apparatus for guiding anesthesia into the subarachnoid space of a patient, the apparatus comprising a base and a guide shaft connected at one end to the base. Another end of the guide shaft may include a non-piercing tip, which is adapted to press against the wall of the dura without penetration thereof. The guide shaft may include a lumen for guiding anesthesia into the dura. A first needle, having a hollow shaft and a bevel point for reaching the epidural space of the patient, may be provided. The hollow shaft of the first needle may have an interior diameter which is adapted to permit insertion of the guide shaft into the hollow shaft of the needle. Anesthesia carrying means which is adapted to be inserted within the lumen of the guide shaft may include a penetrating point for penetrating the wall of the dura. The anesthesia carrying means may also include a hollow interior for transporting anesthesia into the dura. The anesthesia carrying means may comprise a second needle. The second needle may include a bevel point for penetrating the arachnoid into the CSF in the subarachnoid space. Alternatively, the anesthesia carrying means may comprise a catheter assembly. The catheter assembly may comprise a catheter, and a stylet positioned within the catheter. The stylet may at one end include a curved non-cutting pencil point which is capable of spreading apart the filaments of the wall of the dura and guide the catheter after the perforation in the selected direction (e.g., caudally or cranially).

The embodiment of the present invention in which the anesthesia carrying means comprises a catheter assembly may further include a second catheter which has a diameter larger than the first catheter which carries the anesthesia, but smaller than the diameter of the first needle. In the preferred embodiment, after the introducer has been removed, this second catheter is inserted into the first needle over the first catheter until it reaches the dura.

Furthermore, the present invention is a method or an apparatus for irritating the opening or puncture created in the dura wall such that the surface of the dura wall forming the hole becomes inflamed to promote healing of the puncture.

BRIEF DESCRIPTION OF THE DRAWINGS

The foregoing and other objects, aspects and features of the present invention will be more fully appreciated as the same becomes better understood when considered in conjunction with the detailed description of the present invention viewed in conjunction with the accompanying drawings in which:

FIG. 3 is a sectional view showing the apparatus of FIG. 1 in use;

FIG. 4 is a sectional view showing the apparatus of FIG. 2 in use;

FIG. 4A is a sectional view similar to FIG. 4 with a catheter advanced over a stylet;

FIG. 4B is a sectional view similar to FIG. 4A with the stylet removed; and

FIG. 4C is a sectional view similar to FIG. 4A with the first catheter advanced over the stylet and a second catheter positioned over the first catheter.

DETAILED DESCRIPTION OF THE PREFERRED EMBODIMENTS

Figure 1:
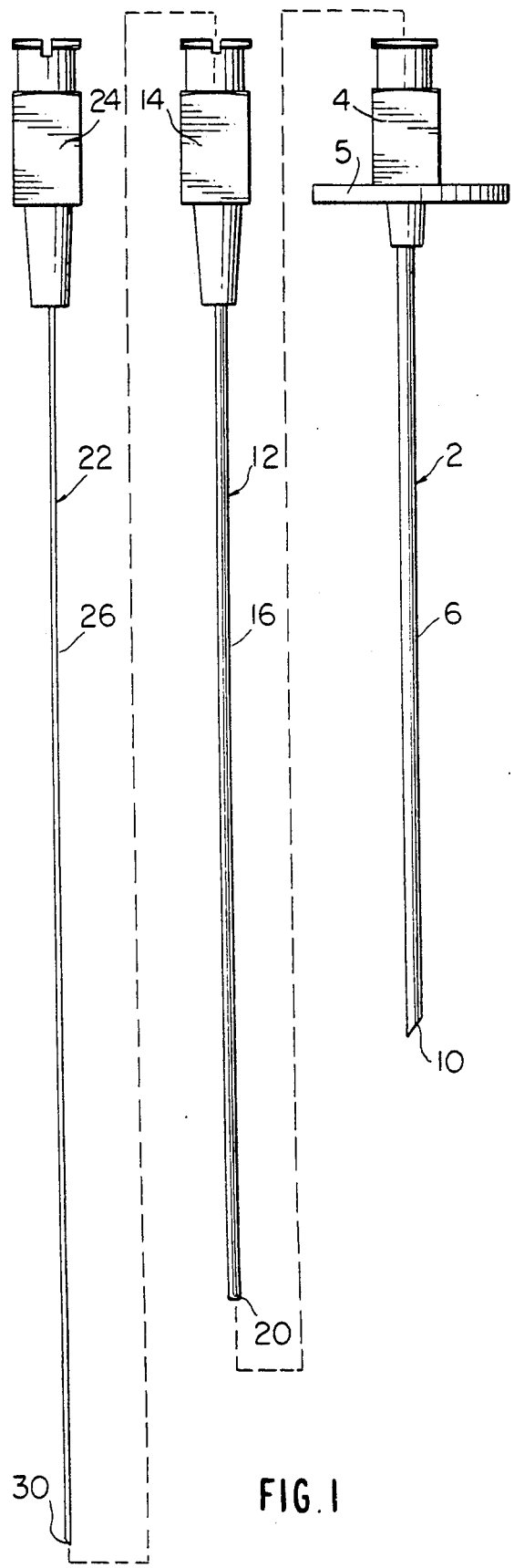
FIG. 1 is an exploded view of the apparatus of the present invention for administering anesthesia through a relatively small gauge needle.

Referring now to the drawings, in which similar reference numerals have been used to refer to similar elements, two preferred embodiments of the present invention are shown. The present invention comprises two related procedures and apparatus for administering anesthesia to a patient (patient, as used herein, refers to both human and animal species). The first apparatus and procedure administers anesthesia in a single dosage via a very small gauge needle and/or epidural catheter. The second apparatus and procedure allows continuous administration of anesthesia via a very small gauge microcatheter. Both apparatus and their attendant procedures reduce the incidence of spinal headache by making a very small, preferably no greater than a 28-gauge, opening through the dura. As discussed in greater detail below, when the epidural catheter is used, the likelihood of the catheter subsequently passing through the tiny opening in the dura created by the spinal needle is significantly reduced. Furthermore, the present invention includes the provision of an introducer, described in more detail below, which helps to guide and to stabilize the instrument creating the opening, i.e., the needle or catheter, as it is being inserted into the dura of the patient.

Turning first to FIG. 1 in which the apparatus for administering a single dosage of anesthesia is shown.

The apparatus generally comprises three basic components: a modified epidural or first needle shown generally at 2, an introducer shown generally at 12, and a spinal or second needle shown generally at 22, each of which will now be described in more detail.

Modified epidural needle or trocar 2 comprises a hollow shaft 6, one end of which is attached to a base 4. Base 4 includes a hand support 5 arranged perpendicularly to base 4 for bracing the hand of the administering professional during insertion of needle 2. The other end of shaft 6 has a dull, bevel point 10 for piercing the skin of the patient. Shaft 6 is hollow, defining interior lumen 8 (FIG. 3) through which introducer 12 and spinal needle 22 are inserted, as discussed below. Epidural needle 2 is within the range of 16-20 gauge, and is preferably a 17-gauge needle. However, a larger or smaller gauge needle may be used, so long as the interior lumen is of sufficient diameter to allow passage of introducer 12 and spinal needle 22.

With continuing reference to FIG. 1, introducer 12 is shown. Introducer 12 comprises a hollow guide shaft 16 defining interior lumen 18 through which spinal needle 22 is inserted, as described below. One end of shaft 16 is attached to a base 14. The other or distal end of shaft 16 presents a non-piercing tip 20. Preferably, tip 20 comprises a rounded edge, however, if tip 20 is of material which is not sharp tip 20 need not be rounded. One advantage of having the distal end of shaft 16 present a non-piercing tip is that when introducer 12 is inserted through epidural needle 2, tip 20 extends beyond point 10 (approximately 0.8 cm) into the epidural space 40 (FIGS. 3 and 4), of the patient. By making tip 20 rounded, it will not pierce the dura wall but will safely press against the wall to act as a guide for spinal needle 22, as will be described in detail below. Introducer 12 is preferably within the range of approximately 18 gauge to 22 gauge and is preferably 19 gauge. Thus, the exterior diameter of shaft 16 is smaller than the interior of epidural needle shaft 6, allowing introducer 12 to be telescopically inserted within epidural needle 2.

With continuing reference to FIG. 1, spinal needle 22 is shown, which is adapted to be inserted within lumen 18 of introducer 12. Spinal needle 22 comprises a hollow shaft 26 terminating in one end at a base 24 and at its other or distal end in a penetrating bevel point 30. Point 30 extends beyond tip 0.20 (approximately 0.5 cm) when needle 22 is fully inserted within introducer 12. Hollow shaft 26 defines interior lumen 28 (FIG. 3), which allows transport of anesthesia through spinal needle 22 to point 30 for administration into the dura, as described below. Spinal needle 22 is approximately 26 gauge to 32 gauge, and is preferably 28-30 gauge. Needles of such fine gauge have caused problems in the past because they are very flexible and difficult to position. Introducer 12 therefore, serves to support and guide needle 22 into the wall of the dura.

In addition to providing a single dosage of anesthesia, epidural needle 2 of this apparatus may also be used to introduce a standard epidural catheter into the epidural space after the spinal needle has been inserted and removed. The details of this procedure are discussed in greater detail below.

Epidural needle 2, introducer 12, and spinal needle 22 are all preferably constructed of stainless steel or other similar material which is suitable for sufficient sterilization for use in medical procedures. Alternatively they may be disposable. Base 4, base 14, and base 24 as shown in FIG. 1 are of a configuration, which is known in the art as a convenient means for securing complex needles into a unified structure, and forms no part of the present invention. The particular length of needle 2, introducer 12 and needle 22 may be other than that shown, as the drawings are merely for illustrative purposes only. However, needle 2 should be of sufficient length to adequately reach the epidural space. Similarly, introducer 12 should be longer than needle 2 and of sufficient length to press against the dura wall. Spinal needle 22 should be longer than introducer 12, and of sufficient length to adequately reach the subarachnoid space.

Figure 2:
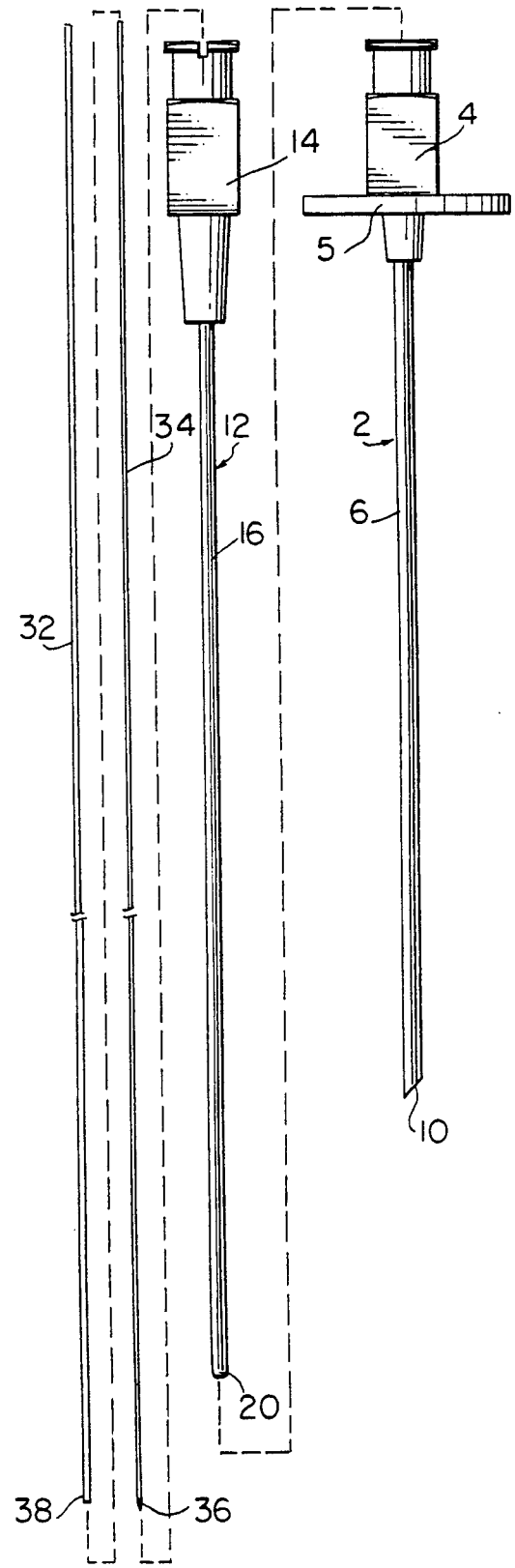
FIG. 2 is an exploded view of the apparatus of the present invention for administering anesthesia through a relatively small gauge catheter.

Turning now to FIG. 2 in which the apparatus of the present invention for administering an infinite dosage of anesthesia via an indwelling microcatheter is shown. As with the first embodiment described above, this embodiment also utilizes modified epidural needle 2 and introducer 12, which are identical to those elements described above. However, in this embodiment, rather than provide spinal needle 22, the anesthesia is administered to the patient via a catheter assembly, preferably consisting of first catheter 32 and stylet 34. Catheter 32 is adapted to be inserted through lumen 18 of introducer 12. Catheter 32 has an open insertion end 38, which is inserted into the dura, and a distal end (not shown). Catheter 32 is approximately 27 gauge to 29 gauge, and is preferably tubing of 28 gauge. Catheter 32 is constructed of nylon or other similarly suitable material which may be sterilized and safely used during medical procedures. Furthermore, the particular material used must be compatible with, and not likely to be rejected by, the patient's body during use. Preferably, the entire length of catheter 32 is approximately 12 to 13 inches. In order to reach the subarachnoid space, as well as to provide stability to catheter 32 as it is inserted through introducer 12 and into the subarachnoid space, a thin wire-like stylet 34, preferably 29 gauge and constructed of stainless steel, is provided within catheter 32. Stylet 34 is preferably solid and includes a non-cutting pencil point 36 at one end which effectively spreads the filaments of the dura wall to allow directed insertion of catheter 32, as described below. Furthermore, it may be desirable to pre-curve point 36 of stylet 34 so that catheter 32 passes more easily through the dura into the subarachnoid space (FIG. 4). For example, the distal 2.0 cm of point 36 may be curved up to approximately 90°. An important feature of pencil point 36 is that it does not puncture the filaments of the dura. Thus, when catheter 32 is removed, the filaments may return to their original position, effectively sealing the opening. This result may have a significant effect in reducing the incidence of spinal headache.

In addition, a second catheter 50 (FIG. 4C) may be provided which is larger in interior diameter than first catheter 32, and smaller in exterior diameter than epidural needle 2. Catheter 50 is preferably, approximately 18-22 gauge and approximately 12 to 15 inches in length. As described in greater detail below, second catheter 50 may be inserted into first needle 2 after introducer 12 is removed. Second catheter 50, preferably constructed of nylon, provides an armored protection to first catheter 32 to help maintain its placement and to assist in removal of catheter 32.

Referring now to FIGS. 3 and 4, where the apparatus of FIGS. 1 and 2 respectively are shown in use, the two apparatus initially function similarly; that is, both apparatus initiate administration by the insertion of epidural needle 2 at a slight angle into the patient's skin until point 10 passes through the ligamentum flavum or ligament L and into the epidural space 40. A stylet, not shown, may be in place within lumen 8 to prevent shaft 6 from being clogged by body tissue. When the resistance of ligament L is perceived, the stylet would be removed. The attendant lack of resistance, once needle 2 has penetrated the ligament L, confirms that the epidural space 40 has been reached. Once the epidural space has been reached by point 10 of needle 2, introducer 12 is inserted through lumen 8 of needle 2. Introducer 12 is carefully forced through lumen 8 until the resistance of dura wall 42 is perceived. Because tip 20 is rounded, introducer 12 will not pierce the dura 42 but, rather, will safely press against it confirming its location. The epidural needle 2 is then withdrawn carefully, while the introducer 42 is kept in position until both epidural needle 2 and introducer 12 are locked together. The introducer 12 is then in stable position, because the epidural needle 2 is fixed in the ligamentum flavum L.

Once introducer 12 is in place, spinal needle 22 is inserted through lumen 18 of introducer 12. Point 30 of needle 22 penetrates the dura 42 and enters the subarachnoid space 44. A syringe (not shown) is connected to base 24, and a gentle suction is applied until spinal fluid within the dura is obtained, confirming the location of point 30. Anesthesia, provided in another syringe (not shown), may then be passed directly into the subarachnoid space 44 through spinal needle 22. Thus, in summary of this procedure, epidural space 40, between ligament L and dura 42, is reached by a relatively large needle 2; introducer 12 is inserted through lumen 8 of needle 2 to press upon the dura 42 and fixed against the ligamentum flavum L; spinal needle 22 is inserted through lumen 18 of introducer 12 to penetrate the dura 42. As spinal needle 22 is of a very fine gauge, i.e., approximately 28 gauge, the hole made in the dura 42 by point 30 of spinal needle 22 is also of a very fine diameter, thus significantly reducing the likelihood of spinal headache, as previously described.

Once the spinal needle 22 and introducer 12 have been removed, a standard epidural catheter may be introduced into the epidural space through epidural needle 2, allowing additional anesthesia to be supplied to the epidural space. This unique arrangement provides the option of using spinal anesthesia for induction, and epidural anesthesia to maintain an anesthetized state. Moreover, as mentioned above, the likelihood that the epidural catheter will be subsequently passed through the opening created in the dura by needle 22 is significantly reduced because of the very small size of the opening created in the dura.

Turning now to the procedure in which spinal anesthesia may be administered to a patient via a very fine gauge catheter, the initial procedure is identical to that described above. That is, the epidural space 40 is reached with modified epidural needle 2. A stylet (not shown), may be provided within lumen 8 to prevent clogging. When then resistance of ligament L is perceived, indicating that epidural space 40 has been reached by point 10 of needle 2, the stylet is removed and introducer 12 is inserted through lumen 8. Introducer 12 is gently inserted until tip 20 presses against the dura wall. Again, since tip 20 is rounded, introducer 12 will not pierce the dura.

While introducer 12 is in position with tip 20 safely pressing against the dura 42, catheter 32 with stylet 34 in place is inserted through lumen 18 of introducer 12. Pencil point 36 of stylet 34 extending just slightly from insertion end 39 of catheter 32 penetrates the dura 42 by spreading the filaments of the dura wall apart (FIG. 4). Both catheter 32 and stylet 35 are then advanced about 1.5 cm so that the pre-curved tip of the stylet 36 is heading caudally or cranially as suggested. The stylet 34 is then locked in position and the catheter 32 is advanced over the point 36 into the subarachnoid space (FIG. 4A). Alternatively, the catheter 32 and stylet are advanced into the subarachnoid space as a unit to the desired position. Stylet 34 is then removed, and a syringe is connected to the distal end of catheter 32. A gentle suction is made until spinal fluid is obtained, confirming location of the insertion end 38 of catheter 32. Epidural needle 2 and introducer 12 are then removed, leaving only catheter 32 in place within the body (FIG. 4B). Distal end of catheter 32 maintained, outside the body, may then be coupled to standard tubing which is connected to a source of anesthesia. The anesthesia may then be administered directly into the subarachnoid space 44 through catheter 32 in intermittent injections at any time during the surgical procedure and thereafter while catheter 32 remains in place.

If second catheter 50 is used to support first catheter 32, it is inserted into the epidural needle 2 after introducer 12 is removed. With particular reference to FIG. 4C, second catheter 50 is slipped over first catheter 32. Once second catheter 50 is in place with its distal end 52 against the dura 42, stylet 34 and needle 2 may be removed and the anesthesia may be administered. Alternatively, stylet 34 could be removed prior to passing second catheter 50 over first catheter 32. Upon completion of the administration, the first catheter 32 and second catheter 50 are withdrawn as a unit. The second catheter supports the first catheter and minimizes the first catheter's propensity to kinking and breaking.

Therefore, in summary, the second procedure of the present invention involves reaching the epidural space 40 between ligament L and dura 42 by a relatively large needle 2; inserting introducer 12 through lumen 8 of needle 2 until tip 20 gently presses upon dura wall 42; and inserting catheter 32, with pencilpointed, internal stylet 34, into lumen 18 of introducer 12, until point 36 of stylet 34 penetrates the dura 42; advancing catheter 32 into the subarachnoid space caudally or cranially, as suggested; removing stylet 34, introducer 12 and epidural needle 2 leaving only catheter 32 in place within the subarachnoid space 44; and administering anesthesia through catheter 32. As stylet 34 includes pencil point 36 and does not puncture the dura wall, the likelihood of spinal headache is significantly reduced, as previously described.

As a further means of reducing the incidence of spinal headache, a substance which promotes healing may be applied to the surface of the dura wall forming the opening through which the epidural needle 30 or first catheter 32 are introduced. The substance may take the form of a granule of conventional styptic, an antibiotic, or a biosubstance such as bicarbonate. Preferably, the substance is a proteinaceous plug of fibrin, a natural clotting material found in the body of an animal (human or otherwise). The advantage of fibrin is that it is unlikely to cause an allergic reaction in the patient. Alternatively, the commercially available sponge form plasma expander, hemostasis GELFOAM by the Upjohn Company, Kalamazoo, Michigan, could also be used.

In the first embodiment, a suitable amount (e.g., one granule) of the protein substance would be applied to the distal end of a metal or plastic rod. The rod would have a diameter smaller than the lumen 18 of introducer 12 and about the same length or slightly shorter in order to just reach the dura wall. The rod with the substance is inserted through introducer 12 after spinal needle 22 is removed. Introducer 12 ensures that the irritant is applied at precisely the spot where needle 22 entered the dura 42. For use with the second embodiment of the invention, the exterior of first catheter 32 could be coated with the protein substance along its length in the area where the cathether is positioned against the dura wall. While the catheter is indwelling, the substance would be rubbed off the catheter onto the dura adjacent the hole created by the catheter. Upon eventual removal of the catheter, the inflammation caused by the irritant would promote healing of the dura wall.

It should be understood by those skilled in the art that the second embodiment in particular of the present invention has applicability other than as an apparatus and procedure for administering anesthesia. That is, that embodiment may be used in any medical procedure in which it is desired to insert a very fine gauge catheter into the body of a patient. Such a catheter may transport medicine other than anesthesia for long-term medical treatment such as pain management. It is also possible to obtain repetitive liquid samples through the catheter for further investigation if necessary.

The principles, preferred embodiments, and modes of operation of the present invention have been described in the foregoing specification. The invention which is intended to be protected herein should not, however, be construed as limited to the particular forms disclosed, as these are to be regarded as illustrative rather than restrictive. Variations in changes may be made by those skilled in the art without departing from the spirit of the invention. Accordingly, the foregoing detailed description should be considered exemplary in nature and not limited to the scope and spirit of the invention as set forth in the attached claims.

What is claimed is:

1. An apparatus for administering fluid into the subarachnoid space of a patient, comprising:
    a first needle having a lumen and a pointed tip, said first needle being of a first length for insertion into the epidural space of the patient without penetration of the dura;
    an introducer having a hollow shaft and a non-piercing tip, said introducer having an exterior diameter smaller than the interior diameter of said lumen of said first needle, such that said introducer is removably inserted through said lumen of said first needle, said introducer being of a second length longer than said first length of said first needle such that the tip of said introducer extends beyond the tip of said first needle to press against the wall of the dura without penetration thereof to place the dura in tension;
    means for maintaining the non-piercing tip of said introducer extended beyond the pointed tip of said first needle as the non-piercing tip of said introducer presses against the wall of the dura, such that the pointed tip of said first needle is prevented from contacting and penetrating the dura; and
    a fluid carrying means for transporting fluid into the dura of said pointed, said fluid carrying means being of a diameter smaller than that of the interior diameter of said introducer such that said fluid carrying means is removably inserted through said hollow shaft of said introducer and wherein said fluid carrying means has a penetrating point to penetrate the dura for administering fluid thereto.

2. An apparatus as set forth in claim 1, wherein the exterior diameter of said introducer is approximately 18 to 22 gauge.

3. An apparatus as set forth in claim 1, wherein said fluid carrying means comprises:
    a catheter assembly, said catheter assembly including a catheter having a hollow interior for transporting said fluid.

4. An apparatus as set forth in claim 3, wherein the exterior diameter of said catheter is approximately 27 to 29 gauge.

5. An apparatus as set forth in claim 1, wherein the exterior diameter of said first needle is approximately 16 to 20 gauge.

6. An apparatus as set forth in claim 1, wherein said non-piercing tip of said introducer is rounded.

7. An apparatus as set forth in claim 3, further comprising a second catheter having an interior diameter larger than said first catheter and smaller than said first needle such that said second catheter may be inserted through said first needle over said first catheter for supporting said first catheter.

8. An apparatus as set forth in claim 1, further comprising:
    a rod having a distal end and a diameter smaller than the interior diameter of said introducer; and
    an irritant disposed on said distal end of said rod, said rod being removably inserted through said introducer upon removal of said fluid carrying means for applying said irritant to said body to promote healing.

9. An apparatus as set forth in claim 3, further comprising:
    an irritant disposed on an exterior surface of said catheter for promoting healing of said patient.

10. A method of administering fluid into a body, comprising the steps of:
    inserting a needle into the body, said needle having a lumen;
    inserting an introducer into said lumen of said needle, said introducer having a hollow shaft and a non-piercing tip;
    guiding a fluid carrying means having a penetrating point into the body by inserting said fluid carrying means into said hollow shaft of said introducer;
    causing said penetrating point to penetrate a desired region of the body;
    verifying the placement of said penetrating point;
    coupling said fluid carrying means to a fluid source; and
    administering said fluid into the body.

11. A method as set forth in claim 10, further comprising the steps of:
    removing said needle from the body; and
    removing said introducer from the body after said needle has been removed.

12. A method as set forth in claim 11, further comprising the step of:
    continuing to administer fluid into said body after said needle and said introducer have been removed.

13. A method as set forth in claim 10, further comprising the steps of
    removing said introducer from said needle; and inserting a catheter into said needle over said fluid carrying means to support said fluid carrying means.

14. A method as set forth in claim 10, further comprising the step of:
removing said fluid carrying means from the body;
inserting a rod having an irritant disposed on its distal end through said introducer after said fluid carrying means has been removed; and
applying said irritant to the penetrated region of the body to promote healing.

15. A method as set forth in claim 10, further comprising the step of:
applying an irritant to the exterior of said fluid carrying means adjacent an area along said fluid carrying means which contacts the penetrated region of the body to promote healing.

16. An apparatus for guiding anesthesia into the subarachnoid space of a patient, comprising:
a first needle having a lumen and a pointed tip for insertion into the epidural space of the patient without penetration of the dura;
a guide shaft which is removably inserted within the lumen of said first needle, said guide shaft having a lumen and a nonpiercing tip, said non-piercing tip of said guide shaft adapted to extend beyond the pointed tip of said first needle to press against the wall of the dura to place the wall in tension without penetration thereof;
means for maintaining the non-piercing tip of said guide shaft extended beyond the tip of said first needle as the non-piercing tip of said guide shaft presses against the wall of the dura, such that the pointed tip of said first needle is prevented from contacting and penetrating the wall of the dura; and
anesthesia carrying means which is removably inserted within said lumen of said guide shaft, said anesthesia carrying means including a penetrating point for penetrating the wall of the dura, said anesthesia carrying means also including a hollow interior for transporting said anesthesia into the dura.

17. An apparatus as set forth in claim 16, wherein said anesthesia carrying means further comprises a second needle which is removably inserted within said guide shaft.

18. An apparatus as set forth in claim 17, wherein said second needle includes a sharp, bevel point for penetrating a wall of the dura.

19. An apparatus as set forth in claim 17, wherein the exterior diameter of said second needle is approximately 28 to 30 gauge.

20. An apparatus as set forth in claim 16, wherein said anesthesia carrying means comprises a catheter assembly.

21. An apparatus as set forth in claim 20, wherein the exterior diameter of said catheter assembly is approximately 27 to 29 gauge.

22. An apparatus as set forth in claim 20, wherein said catheter assembly comprises:
a first catheter; and
a stylet positioned within said first catheter, said styler having at one end, a noncutting pencil point capable of spreading apart the filaments of a wall of the dura.

23. An apparatus as set forth in claim 22, further comprising:
a second catheter having an interior diameter larger than said first catheter and smaller than said first needle, such that said second catheter may be inserted through said first needle over said first catheter for supporting said first catheter.

* * * * *